United States Patent
Caprotti et al.

(10) Patent No.: US 6,293,976 B1
(45) Date of Patent: Sep. 25, 2001

(54) LUBRICITY ADDITIVES FOR FUEL OIL COMPOSITIONS

(75) Inventors: Rinaldo Caprotti; Christophe Le Deore, both of Oxford (GB)

(73) Assignee: Infineum USA L.P., Linden, NJ (US)

( * ) Notice: Subject to any disclaimer, the term of this patent is extended or adjusted under 35 U.S.C. 154(b) by 0 days.

(21) Appl. No.: 09/284,174

(22) PCT Filed: Sep. 15, 1997

(86) PCT No.: PCT/EP97/05106

§ 371 Date: Jul. 15, 1999

§ 102(e) Date: Jul. 15, 1999

(87) PCT Pub. No.: WO98/16600

PCT Pub. Date: Apr. 23, 1998

(30) Foreign Application Priority Data

Oct. 11, 1996 (GB) .................................................. 9621261

(51) Int. Cl.⁷ ................................ C10L 1/18; C10L 1/22; C10L 1/24

(52) U.S. Cl. .................. 44/338; 44/340; 44/349; 44/350; 44/419

(58) Field of Search .............................. 44/418, 419, 338, 44/340, 349, 350

(56) References Cited

U.S. PATENT DOCUMENTS

| | | | |
|---|---|---|---|
| 1,938,456 * | 12/1933 | Lankelma | 44/418 |
| 2,070,304 * | 2/1937 | Jaeger | 44/418 |
| 2,848,418 * | 8/1958 | Müller et al. . | |
| 2,959,550 * | 11/1960 | Young et al. . | |
| 3,034,879 * | 5/1962 | Spacht | 44/419 |
| 3,110,670 * | 11/1963 | Nelson . | |
| 3,273,981 | 9/1966 | Furey . | |
| 3,282,939 * | 11/1966 | Spivack | 44/419 |
| 3,287,273 | 11/1966 | Furey et al. . | |
| 3,338,833 * | 8/1967 | Spivack et al. | 44/419 |
| 3,558,552 * | 1/1971 | Spacht | 44/418 |
| 4,090,971 | 5/1978 | Hoke . | |
| 4,902,830 * | 2/1990 | Scholl et al. | 564/155 |
| 5,089,158 | 2/1992 | Van Kruchten et al. . | |
| 5,092,908 * | 3/1992 | Feldman et al. | 44/418 |
| 5,108,462 * | 4/1992 | Habeeb | 44/383 |
| 5,250,081 * | 10/1993 | Habeeb | 44/412 |
| 5,441,544 * | 8/1995 | Cherpeck | 44/418 |
| 5,466,268 | 11/1995 | Cherpeck | 44/419 |
| 5,637,121 * | 6/1997 | Cherpeck | 44/418 |

FOREIGN PATENT DOCUMENTS

| | | |
|---|---|---|
| 465042 | 1/1992 | (EP) . |
| 719761 | 7/1996 | (EP) . |
| 719762 | 7/1996 | (EP) . |
| 1505302 | 3/1978 | (GB) . |
| 2235695 | 3/1991 | (GB) . |
| WO 92/12224 | 7/1992 | (WO) . |
| WO 94/17160 | 8/1994 | (WO) . |
| WO 95/17484 | 6/1995 | (WO) . |
| WO 95/33805 | 12/1995 | (WO) . |
| WO 96/18706 | 6/1996 | (WO) . |

* cited by examiner

*Primary Examiner*—Margaret Medley

(57) ABSTRACT

There are disclosed low sulphur content middle distillate fuel oils which have their lubricity properties greatly improved through the addition of a compound having at least one substituted aromatic ring system wherein the substituents are one or more aliphatic hydrocarbyl groups having 14 to 36 carbon atoms, one or more hydroxyl groups or a derivative thereof and one or more amide groups.

5 Claims, No Drawings

LUBRICITY ADDITIVES FOR FUEL OIL COMPOSITIONS

This application is a 371 of PCT/EP97/05106 dated Sep. 15, 1997.

This invention relates to additives for improving the lubricity of fuel oils such as diesel fuel oil. Diesel fuel oil compositions including the additives of this invention exhibit improved lubricity and reduced engine wear.

Concern for the environment has resulted in moves to significantly reduce the noxious components in emissions when fuel oils are burnt, particularly in engines such as diesel engines. Attempts are being made, for example, to minimise sulphur dioxide emissions. As a consequence attempts are being made to minimise the sulphur content of fuel oils. For example, although typical diesel fuel oils have in the past contained 1% by weight or more of sulphur (expressed as elemental sulphur) it is now considered desirable to reduce the level to 0.2% by weight, preferably to 0.05% by weight and, advantageously, to less than 0.01% by weight, particularly less than 0.001% by weight.

Additional refining of fuel oils, necessary to achieve these low sulphur levels, often results in reductions in the level of polar components. In addition, refinery processes can reduce the level of polynuclear aromatic compounds present in such fuel oils.

Reducing the level of one or more of the sulphur, polynuclear aromatic or polar components of diesel fuel oil can reduce the ability of the oil to lubricate the injection system of the engine so that, for example, the fuel injection pump of the engine fails relatively early in the life of an engine. Failure may occur in fuel injection systems such as high pressure rotary distributors, in-line pumps and injectors. The problem of poor lubricity in diesel fuel oils is likely to be exacerbated by the future engine developments aimed at further reducing emissions, which will have more exacting lubricity requirements than present engines. For example, the advent of high pressure unit injectors is anticipated to increase the fuel oil lubricity requirement.

Similarly, poor lubricity can lead to wear problems in other mechanical devices dependent for lubrication on the natural lubricity of fuel oil.

Lubricity additives for fuel oils have been described in the art. WO 94/17160 describes an additive which comprises an ester of a carboxylic acid and an alcohol wherein the acid has from 2 to 50 carbon atoms and the alcohol has one or more carbon atoms. Glycerol monooleate is specifically disclosed as an example. Acids of the formula "$R^1$(COOH)", wherein $R^1$ is an aromatic hydrocarbyl group are generically disclosed but not exemplified.

U.S. Pat. No. 3,273,981 discloses a lubricity additive being a mixture of A+B wherein A is a polybasic acid, or a polybasic acid ester made by reacting the acid with C1–C5 monohydric alcohols; while B is a partial ester of a polyhydric alcohol and a fatty acid, for example glycerol monooleate, sorbitan monooleate or pentaerythritol monooleate. The mixture finds application in jet fuels.

GB-A-1,505,302 describes ester combinations including, for example, glycerol monoesters and glycerol diesters as diesel fuel additives, the combinations being described as leading to advantages including less wear of the fuel-injection equipment, piston rings and cylinder liners. GB-A-1,505,302 is, however, concerned with overcoming the operational disadvantages of corrosion and wear by acidic combustion products, residues in the combustion chamber and in the exhaust system. The document states that these disadvantages are due to incomplete combustion under certain operating conditions. Typical diesel fuels available at the date of the document contained, for example, from 0.5 to 1% by weight of sulphur, as elemental sulphur, based on the weight of the fuel.

U.S. Pat. No. 3,287,273 describes lubricity additives which are reaction products of a dicarboxylic acid and an oil-insoluble glycol. The acid is typically predominantly a dimer of unsaturated fatty acids such as linoleic or oleic acid, although minor proportions of the monomer acid may also be present. Only alkane diols or oxa-alkane diols are specifically suggested as the glycol reactant.

U.S. Pat. No. 4,090,971 and EP-A-0 719 761 describe certain amides of substituted hydoxyaromatic carboxylic acids, these materials being described as useful as dispersant additives for lubricants and fuels, respectively. No mention is made of low sulphur middle distillate fuels or how to solve their corresponding problem of poor lubricity.

U.S. Pat. No. 5,089,158 describes derivatives of amides of an aromatic carboxylic acid having an ortho-hydroxy group in the form of a salt with a multivalent metal ion, formed from amide precursors via an ester intermediate. The salts so formed are preferably overbased.

There exists in the art a continual need for lubricity additives showing enhanced performance, due not only to the development of engines with more exacting requirements, but also to the general demand from consumers and fuel producers for higher quality fuels.

Furthermore, there is an increasing need in the art for 'multifunctional' additive compositions. Such compositions provide a range of performance-enhancing functions, typically through the incorporation therein of a number of individual additives each having its own function. The resulting complex mixtures often require addition to the fuel in relatively large amounts, and may also suffer from problems of physical and chemical interaction between individual additives which can impair their subsequent performance in the fuel. The provision of an individual additive with multiple performance-enhancing effects can reduce or avoid the need for such complex compositions and their associated problems.

It has now been found that certain amides of specific substituted aromatic carboxylic acids show improved lubricity performance. Some of these amides may also impart other performance-enhancing effects to low-sulphur fuel oils.

In a first aspect, this invention provides a fuel oil composition obtainable by the addition of a minor proportion of a compound comprising one or more aromatic ring systems wherein at least one of the ring systems bears, as substituents;

(i) one or more hydrocarbyl groups imparting oil solubility to the compound, and (ii) one or more hydroxyl groups or derivatives thereof or both, and (iii) one or more amide groups to a major proportion of a liquid hydrocarbon middle distillate fuel oil having a sulphur concentration of 0.2% by weight or less, based on the weight of fuel.

In a second aspect, this invention provides a fuel oil composition obtainable by the addition, to the fuel oil defined under the first aspect, of an additive composition or concentrate into which has been incorporated the compound defined under the first aspect.

In a third aspect, this invention provides a compound comprising one or more aromatic ring systems, wherein at least one of the ring systems bears, as substituents;

(i) one or more hydrocarbyl groups imparting oil solubility to the compound, and (ii) one or more hydroxyl derivatives of the formula —OR' wherein R' is hydrocarbyl or a group of the formula Hydrocarbyl-(M-alkylene)$_n$- wherein M represents an oxygen atom or an NH group and n represents a number from 1 to 50, and (iii) one or more amide groups.

Further aspects of this invention include an additive composition into which has been incorporated the compound of the third aspect, and an additive concentrate obtainable by incorporating the compound or additive composition and optionally one or more additional additives, into a mutually-compatible solvent therefor.

The compounds defined under the first aspect of the invention provide, upon addition to low sulphur middle distillate fuel oil, an improvement in fuel oil lubricity.

In particular, the specific compounds defined under the first aspect, including those compounds claimed under the third aspect, give higher lubricity performance even at treat rates as low as 15 to 50 parts per million by weight, per weight of fuel oil. Furthermore, some of these compounds may impart other performance-enhancing features to fuel oils, particularly detergency of engine fuel inlet systems and especially fuel injectors, reduced oxidation tendency especially during storage, and the ability to disperse insolubles which might otherwise give rise to harmful deposits and/or fuel line blockages. The detergency and dispersancy advantages may be apparent for those components wherein one or more of the substituents (ii) is a derivative of a hydroxyl group of the formula OR' as hereinafter described.

The Fuel Oil Composition of the First Aspect of the Invention

A The Compound

The compound may comprise one or more aromatic ring systems. By 'aromatic ring system' in this specification is mean a planar cyclic moiety which may be an aromatic homocyclic, heterocyclic or fused polycyclic assembly or a system where two or more such cyclic assemblies are joined to one another and in which the cyclic assemblies may be the same or different. It is preferred that the or each aromatic ring system is system based on heterocylic or homocyclic 5- or 6-membered rings, more preferably 6-membered rings and most preferably benzene rings.

The ring atoms in the aromatic system are preferably carbon atoms but may for example include one or more heteroatoms such as N, S, or O in the system in which case the compound is a heterocyclic compound.

Examples of suitable polycyclic assemblies include (a) condensed benzene structures such as naphthalene, anthracene, phenanthrene, and pyrene;

(b) condensed ring structures where none of or not all of the rings are benzene such as azulene, indene, hydroindene, fluorene, and diphenylene;

(c) rings joined "end-on" such as biphenyl; and (d) heterocyclic compounds such as quinoline, indole, 2:3 dihydroindole, benzofuran, benzothiophen, carbazole and thiodiphenylamine.

Where the compound comprises only one aromatic ring system, this system necessarily bears all three types of substituent (i), (ii) and (iii). It is preferred that one of each of the substituents (ii) and (iii) is present in such a compound. It is also preferred that one, two or three substituents (i) are present, at least one of which is capable of imparting oil solubility to the compound.

Where the compound comprises two or more aromatic ring systems, it is preferred that at least two, and preferably each, of the systems bears all three types of substituent (i), (ii) and (iii). It is preferred that each system bearing these three types of substituents bears one of each of substituent (ii) and (iii), and preferably one, two or three substituents (i), subject to the requirement that at least one of the substituents (i) provides oil solubility to the compound.

Particularly preferred are compounds wherein the or each aromatic ring system is a single, 6-membered ring, especially a benzene structure. Most preferably, the compound comprises a single benzene ring and one, two or three (preferably one or two) of the substituents (i) and having one of each of the (ii) and (iii) substituents, wherein substituent (ii) is a hydroxyl group.

Substituent (i) is a hydrocarbyl group. By the term hydrocarbyl in this specification is meant an organic moiety which is composed of hydrogen and carbon, which is bonded to the rest of the molecule by a carbon atom or atoms which unless the context states otherwise, may be aliphatic, including alicyclic, aromatic or a combination thereof. It may be substituted or unsubstituted alkyl, aryl or alkaryl and may optionally contain unsaturation or heteroatoms such as O, N or S, provided that such heteroatoms are insufficient to alter the essentially hydrocarbon nature of the group.

It is preferred that substituent (i) is aliphatic, for example alkyl or alkenyl, which may be branched or preferably straight-chain. Straight-chain alkyl is preferred.

Alternatively substituent (i) may comprise a branched or preferably linear alkyl or alkenyl chain interrupted and/or substituted by one or more oxygen, sulphur or especially nitrogen atoms. Suitable examples include a substituent comprising one or more amino groups and optionally terminated by an amino group. Preferred substituents of this class include straight chain alkyl groups terminally and/or internally-substituted by one or more amino groups; and the substituents obtained from the Mannich-type condensation reaction of an alkylene diamine, aldehyde and the aromatic ring system on which the substituent(i) is required, the reaction resulting in the formation of a substituent(i) of the formula:

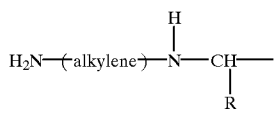

wherein alkylene represents the alkylene segment of the reacting diamine and R represents the substituent stemming from the aldehyde. Thus, for example, when formaldehyde is used in the formation of the above substituent(i), R will represent hydrogen, higher aldehydes resulting in the formation of a corresponding substituent which is preferably alkyl and more preferably straight-chain alkyl.

It is essential for the good performance of the compound that at least one substituent of the formula (i) be a hydrocarbyl group of sufficient oleophilic character to impart oil solubility to the compound. In this respect, it is preferred that at least one substituent (i) contains at least 8 carbon atoms, and preferably 10 to 200 carbon atoms. A substituent having 12 to 54, for example 14 to 36 carbon atoms is particularly preferred. Most preferred are alkyl or alkenyl groups containing 12 to 54 carbon atoms, especially straight chain alkyl groups. The groups having 14 to 20 carbon atoms are most advantageous. Also preferably, such substituent(i) does not contain more than 5 heteroatoms or heteoatom-containing groups and more preferably no more than 3 such atoms or groups, such as 2 such atoms or groups.

Provided that the compound possesses at least one hydrocarbyl substituent (i) imparting the requisite oil solubility, any additional substituents (i) may be of any character provided that they do not adversely interfere with the oil solubility of the compound. Thus, such additional substituents (i) may contain any number of carbon atoms and may also be interrupted by heteroatoms or hetero atom-containing groups, and/or substituted by heteroatom-containing groups. A mixture of compounds differing in such additional substituents (ii) may be used. In particular, such substituents may be derived from alkylene diamines or polyalkylene polyamines via the Mannich type condensation reaction described above; such products can also provide particularly advantageous dispersion and detergent properties to the resulting compounds. Hydroxyl-substituted amines or polyamines can also be used to form compounds having especially good multifunctional activity.

Substituent (ii) is a hydroxyl group or derivative thereof, and can be represented by the formula —OR'. When a hydroxyl group, the compound may show particularly good performance as an oxidation inhibitor.

The hydroxyl group may be derivatised into a substituent capable of imparting other multifuctional character, for example a group of the form —OR' wherein R' is hydrocarbyl as hereinbefore described in relation to substituent (i), or a linear or branched chain alkyleneoxyhydrocarbyl or poly(alkyleneoxy)hydrocarbyl group and/or a linear or branched chain alkyleneaminohydrocarbyl or poly(alkyleneamino)hydrocarbyl group having the formula:

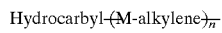

wherein M represents a oxygen atom or an NH group and n represents a number from 1 to 50, preferably 2 to 20, more preferably 2 to 10, for example 3 to 5; and wherein hydrocarbyl is as previously defined and may especially be substituted, preferably terminally substituted, by a heteroatom-containing group, for example a hydroxyl or amino group. Small hydrocarbyl groups, such as those containing 1 to 24, preferably 1 to 18, for example 2 to 12 carbon atoms are particularly advantageous. The alkylene group may contain 1 to 6, for example 2 to 4 methylene units and may also optionally be substituted by such a heteroatom containing group or groups. R' may be bonded directly to the oxygen depending from the ring system or indirectly via a linking group, such as a carbonyl group. The heteroatom-containing derivatives of the hydroxyl group, useful as substituent (ii), may prove particularly beneficial in providing dispersant and/or detergent properties when used in fuel oils. Preferred in this respect are derivatives of the formula —O(CH$_2$)$_{n'}$—NH$_2$ wherein n' represents a number from 1 to 24, preferably 1 to 18, more preferably 1 to 6, particularly 3.

Substituent (iii) is an amide group, wherein the carbonyl carbon of the amide is preferably bonded directly to a ring atom of the aromatic ring system and more preferably to a ring carbon. The amide group is preferably of the formula:

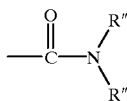

wherein the group —NR"R'" is derivable from the corresponding amine HNR"R'", wherein R" and R'" each independently represent hydrogen or a hydrocarbyl group as previously defined, and especially one having 1 to 30, for example 1 to 22, carbon atoms and optionally substituted by heteroatoms or heteroatom-containing groups, or R" and R'" each independently represent a poly(alkyleneoxy)alkyl or poly(alkyleneamino)alkyl group, also optionally so substituted.

Preferably at least one, and more preferably the or each substituent (iii), is derivable from a primary amine or compound containing at least one primary amine group. Thus, for example, where the substituent (iii) is of the formula

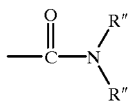

one of the R" and R'" substituents in the amide group is hydrogen. The remaining substituent is preferably a hydrocarbyl group, or an amino-interrupted and/or amino-substituted hydrocarbyl group, wherein the hydrocarbyl group is preferably alkyl, more preferably n-alkyl. Such amides are derivable for example from amines such as hydrocarbyl amines, hydrocarbylene diamines and polyhydrocarbylene polyamines having at least one primary amine group. Other amino groups, where present, may be primary, secondary or tertiary amino groups. Such amines may suitably also be substituted by other heteroatom-containing groups, such as hydroxyl-groups or derivatives thereof.

Particularly good results have been achieved where the amine from which the amide group is derivable is an alkylene diamine. Suitable diamines may contain one or two preferably primary amino groups and between 1 and 50, for example 2 to 10, preferably 2 to 6 carbon atoms preferably in a straight alkylene chain. Where the diamine contains one primary amino group, the other group may be a secondary or tertiary amino group. Especially suitable examples include N,N-dimethyl-1,3-propanediamine; N,N-dimethyl-1,2-propanediamine; N,N-dimethyl-1,2-ethanediamine; and their N,N-diethyl and N,N-dipropyl substituted homologues. N,N-dimethyl-1,3-propanediamine is most preferred.

Where the diamine contains two primary groups, especially suitable examples include 1,2-ethanediamine; 1,2- and 1,3-propanediamines; and 1,2-, 1,3- and 1,4-butanediamines. 1,2-ethanediamine is most preferred.

Particularly good results have also been achieved where the amine from which the amide group is derivable is a polyalkylene polyamine. Suitable amines include those containing one or two amino groups and between 2 and 50, for example 4 and 20 carbon atoms, and preferably between 6 and 12 carbon atoms, preferably in a series of straight alkylene segments. Such amines include those of the general formula

wherein alkylene represents a straight chain alkylene segment containing preferably 2 to 4 carbon atoms, and x represents a number from 2 to 10, preferably 3 to 6. Mixtures of such polyalkylene polyamines, as are typically produced commercially, may be used to good effect. Such mixtures may also additionally contain polyamines in which 'alkylene' may represent branched chain or cyclic units.

Particularly suitable polyalkylene polyamines are polyethylene polyamines such as diethylene triamine; triethylene tetramine; tetraethylene pentamine and pentaethylene hexamine, and mixtures thereof. Mixtures are typically described by reference to the polyamine to which their average composition approximates; thus, 'a mixture approximating to tetraethylene pentamine' is one in which the average number of nitrogens per molecule of polyamine approximates to 5. Triethylene tetramine, tetraethylene pentamine and pentaethylene hexamine are most preferred as amine materials useful for forming the amides of this invention, with pentamine mixtures being most highly preferred.

Polypropylene and polybutylene polyamine analogues, and mixtures thereof, are also suitable amines for forming the amides used in this invention.

Other useful amines are polyhydroxyamines giving rise in the compound to amide groups comprising hydroxy-substituted alkyl substituents. Suitable polyhydroxy amines are aliphatic, saturated or unsaturated, straight chain or branched hydroxy amines having 2 to 10, preferably 2 to 6, more preferably 2 to 4, hydroxyl groups, and having 2 to 90, preferably 2 to 30, more preferably 2 to 12, most preferably 2 to 5, carbon atoms in the molecule.

In the compound, the substituents (ii) and (iii) are preferably positioned vicinally on the aromatic ring system from which they depend. Where the system is polycyclic they are preferably positioned vicinally on the same ring of the polycylic system, for example in an ortho position to each other, although they may be positioned on different rings. The or each substituent (i) may be positioned vicinally to any of the substituents (ii) or (iii), or in a position further removed in the ring system.

The compound may also be of oligomeric structure, for example a series of aromatic ring systems connected via alkylene bridges produced, for example, by the phenol-formaldehyde type condensation reaction of several aromatic ring systems with an aldehyde; or an oligomer containing two or more aromatic ring systems in which each ring is amidated to a different nitrogen of the same di- or polyamine. Particularly useful are methylene-bridged compounds wherein each aromatic ring system is preferably a homocyclic, six-membered ring and wherein, more preferably, each ring carries at least one of each of the substituents (i), (ii) and (iii).

A preferred form of the compound can be represented by the following general formula (I):

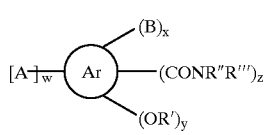

(I)

wherein Ar represents an aromatic ring system, —B, —OR' and —CONR"R''' represent substituents (i), (ii) and (iii) respectively as hereinbefore defined, and A represents a group of the formula (II):

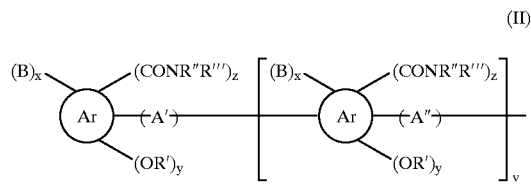

(II)

wherein Ar, B, R', R" and R''' are as hereinbefore defined in formula (I) and

A' and A" each independently represent hydrocarbylene groups, and wherein:

v represents an integer in the range of from 0 to 10;

w represents an integer in the range of from 0 to 3;

and x, y and z each independently represent an integer in the range of from 1 to 3.

Preferably, R' represents hydrogen, or a hydrocarbyl group, or a poly(alkyleneoxy)alkyl or poly(alkyleneamino)alkyl group optionally substituted by one or more heteroatom-containing groups, and wherein R' may be bonded either directly to the oxygen depending from the ring system, or indirectly via a linking group; R" and R''' preferably independently represent hydrogen or a hydrocarbyl group optionally substituted by one or more heteroatom-containing groups, or a poly(alkyleneoxy) alkyl or poly(alkyleneamino)alkyl group, also optionally so substituted, or other preferments of R" and R''' described hereinbefore.

Preferably, x represents 1 or 2, especially when y and z each represent 1. When w is 1 to 3, v is preferably 1 to 9, for example 2 to 5, such as 3. Alternatively, v maybe 0 (zero). A' and A" are preferably methylene or substituted methylene groups.

When w=o, the compound comprises a single aromatic ring system having substituents (i), (ii) and (iii). It is preferred that when w=o, y and z each=1 and x=1 or 2; more preferably, R" represents an alkyl, alkylene amino or poly-alkylenepolyamino group and R' and R''' represent hydrogen. Most preferably, Ar represents a benzene ring; w=0; x=1 or 2; y and z each=1; R" represents a alkyl group and R' and R''' represent hydrogen.

Most preferably, the compound is the ethane-1,2-diamine or tetraethylene pentamine amide of alkyl-substituted salicylic acid, the alkyl substituent or substituents of the acid containing between 14 and 18 carbon atoms.

The mechanism of action of the compound is not clearly understood. However, it is postulated that the specific substituted aromatic ring system or systems form a flat region within the molecule, the hydroxyl or hydroxyl-derivatised group and the amide group and substitutents of said group contributing to an electronic and polar character across this flat region which is surprisingly effective at surface adsorption and improving the fuels' ability to lubricate critical metal surfaces in the injection system, and particularly in the injection pump.

The compound may be prepared by conventional means. Thus, for example, the compound may be prepared by amidification of a precursor compound having the requisite aromatic ring system or systems bearing substituent(s) (i), substituent(s) (ii) and one or more carboxylic acid substituents, or acylating derivatives thereof, capable of amidification with compounds having at least one amino group to form substituent (iii). Suitable acylating derivatives include esters, anhydrides and acid halides.

A suitable method for the preparation of the amides is described in U.S. Pat. No. 4,090,971, column 5, line 34 to column 6, line 25, the disclosure of which method forms part of the description of this invention.

The precursor compound may itself be prepared by hydrocarbylation of a suitable hydroxy-substituted aromatic ring system compound, for example by an electrophilic substitution reaction using a halide derivative of the desired hydrocarbyl substituent(s), for example via a Friedel-Crafts type reaction using iron (iii) chloride as catalyst. Alternatively, hydrocarbylation can be achieved through reaction of the corresponding alkene using a hydrogen fluoride and boron trifluoride catalyst system, or hydrogen chloride and aluminium trichloride catalyst system. The resulting hydrocarbyl-substituted, hydroxy-substituted aromatic compound may be carboxylated, for example via the 'Kolbe-Schmitt' reaction comprising the reaction of a salt, preferably an alkali metal salt, of the hydrocarbyl substituted, hydroxy-substituted aromatic compound with carbon dioxide and subsequently acidifying the salt thus obtained. Alternatively, a Friedel-Crafts acylation-type reaction product may be used to add the required carboxylic acid substituent(s). This acid may be derivatised into an acylating group such as an ester group, anhydride group or acid halide group, for example an acid chloride group, order to facilitate the subsequent amidification reaction. The above types of reaction are well-known in the chemical art.

The preferred precursor compounds are carboxylic acid derivatives of hydrocarbyl-substituted phenols and/or napthols, with phenols being the most preferred. Particularly preferred are the hydrocarbyl-substituted salicylic acids, which typically comprise a mixture of mono and disubstituted acids. These materials are readily available in a form suitable for the amidification reaction, without the need for further modification.

B The Middle Distillate Fuel Oil

The fuel oil has a sulphur concentration of 0.2% by weight or less based on the weight of the fuel, and preferably 0.05% or less, more preferably 0.03% or less, such as 0.01% or less, most preferably 0.005% or less and especially 0.001% or less. Such fuels may be made by means and methods known in the fuel-producing art, such as solvent extraction, hydrodesulphurisation and sulphuric acid treatment.

As used in this specification, the term "middle distillate fuel oil" includes a petroleum oil obtained in refining crude oil as the fraction between the lighter kerosene and jet fuels fraction and the heavier fuel oil fraction. Such distillate fuel oils generally boil within the range of about 100° C., eg 150° to about 400° C. and include those having a relatively high 95% distillation point of above 360° C. (measured by ASTM-D86). In addition, "city-diesel" type fuels, having lower 95% distillation point of 260–330° C. and particularly also sulphur contents of less than 200 ppm, preferably 50 ppm and particularly 10 ppm (weight/weight) are included within the term 'middle distillate fuel oil'.

Middle distillates contain a spread of hydrocarbons boiling over a temperature range, including n-alkanes which precipitate as wax as the fuel cools. They may be characterised by the temperatures at which various %'s of fuel have vaporised ('distillation point'), e.g. 50%, 90%, 95%, being the interim temperatures at which a certain volume % of initial fuel has distilled. They are also characterised by pour, cloud and CFPP points, as well as their initial boiling point (IBP) and 95% distillation point or final boiling point (FBP). The fuel oil can comprise atmospheric distillate or vacuum distillate, or cracked gas oil or a blend in any proportion of straight run and thermally and/or catalytically cracked distillates. The most common middle distillate petroleum fuel oils are diesel fuels and heating oils. The diesel fuel or heating oil may be a straight atmospheric distillate, or it may contain minor amounts, e.g. up to 35 wt %, of vacuum gas oil or cracked gas oils or of both.

Heating oils may be made of a blend of virgin distillate, eg gas oil, naphtha, etc and cracked distillates, eg catalytic cycle stock. A representative specification for a diesel fuel includes a minimum flash point of 38° C. and a 90% distillation point between 282 and 380° C. (see ASTM Designations D-396 and D-975).

As used in this specification, the term 'middle distillate fuel oil' also extends to biofuels, or mixtures of biofuels with middle distillate petroleum fuel oils.

Biofuels, ie fuels from animal or vegetable sources are believed to be less damaging to the environment on combustion, and are obtained from a renewable source. Certain derivatives of vegetable oil, for example rapeseed oil, eg those obtained by saponification and re-esterification with a monohydric alcohol, may be used as a substitute for diesel fuel. It has recently been reported that mixtures of biofuels, for example, between 5:95 and 10:90 by volume are likely to be commercially available in the near future.

Thus, a biofuel is a vegetable or animal oil or both or a derivative thereof.

Vegetable oils are mainly triglerides of monocarboxylic acids, eg acids containing 10–25 carbon atoms and of the following formula:

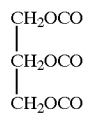

wherein R is an aliphatic radical of 10–25 carbon atoms which may be saturated or unsaturated.

Generally, such oils contain glycerides of a number of acids, the number and kind varying with the source vegetable of the oil.

Examples of oils are rapeseed oil, coriander oil, soyabean oil, cottonseed oil, sunflower oil, castor oil, olive oil, peanut oil, maize oil, almond oil, palm kernel oil, coconut oil, mustard seed oil, beef tallow and fish oils. Rapeseed oil, which is a mixture of fatty acids particularly esterified with glycerol, is preferred as it is available in large quantities and can be obtained in a simple way by pressing from rapeseed.

Examples of derivatives thereof are alkyl esters, such as methyl esters, of fatty acids of the vegetable or animal oils. Such esters can be made by transesterification.

As lower alkyl esters of fatty acids, consideration may be given to the following, for example as commercial mixtures: the ethyl, propyl, butyl and especially methyl esters of fatty acids with 12 to 22 carbon atoms, for example of lauric acid, myristic acid, palmitic acid, palmitoleic acid, stearic acid, oleic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Mixtures with particularly advantageous properties are those which contain mainly, ie. to at least 50 wt % methyl esters of fatty acids with 16 to 22 carbon atoms and 1, 2 or 3 double bonds. The preferred lower alkyl esters of fatty acids are the methyl esters of oleic acid, linoleic acid, linolenic acid and erucic acid.

Commercial mixtures of the stated kind are obtained for example by cleavage and esterification of natural fats and oils by their transesterification with lower aliphatic alcohols. For production of lower alkyl esters of fatty acids it is advantageous to start from fats and oils with high iodine number, such as, for example, sunflower oil, rapeseed oil, coriander oil, castor oil, soyabean oil, cottonseed oil, peanut oil or beef tallow. Lower alkyl esters of fatty acids based on a new variety of rapeseed oil, the fatty acid component of which is derived to more that 80 wt % from unsaturated fatty acids with 18 carbon atoms, are preferred.

The above described biofuels may be used in blends with middle distillate petroleum fuel oils. Such blends typically contain 0 to 10% by weight of the biofuel and 90 to 100% by weight of the petroleum fuel oil, although other relative proportions may also be used to advantageous effect. Particularly useful are blends of biofuels with 'city-diesel' type fuel oils which exhibit extremely low levels of sulphur and are therefore particularly prone to lubricity problems.

In the fuel oil composition of the first aspect, the concentration of the compound incorporated into the oil may for example be in the range of 0.5 to 1,000 ppm of additive (active ingredient) by weight per weight of fuel, for example 1 to 500 ppm such as 10 to 200 ppm by weight per weight of fuel, preferably 20 to 200 ppm, more preferably 25 to 100 ppm.

In addition to middle distillate fuel oils, other fuels having a need for increased lubricity, such as fuels (e.g. future gasoline) intended for high pressure fuel injection equipment, may suitably be treated with the additives of the invention.

The Fuel Oil Composition of the Second Aspect of the Invention

C The Additive Composition

The additive composition defined under the second aspect is prepared by the incorporation of the compound as defined under the first aspect into a composition itself comprising one or more additives for fuel oils. Such incorporation may be achieved by blending or mixing, either with an existing composition or with the components thereof, to produce the additive. However, the term 'incorporation' within the meaning of this specific atom extends not only to the physical mixing of the compound with other materials, but also to any physical and/or chemical interaction which may result upon introduction of the compound, or upon standing.

Many fuel oil additives are known in the art and may be used to form the additive composition into which the compound is incorporated. Such additives include for example the following; detergents, antioxidants, corrosion inhibitors, dehazers, demulsifiers, metal deactivators, antifoaming agents, cetane improvers, combustion improvers, dyes, package compatibilisers, further lubricity additives and anti-static additives. Cold flow-improving additives may also be present D The Additive Concentrate Composition The concentrate may be obtained by incorporating the compound defined under the first aspect, or the additive composition, into a mutually-compatible solvent therefor. The resulting mixture may be either a solution or a dispersion, but is preferably a solution. Suitable solvents include organic solvents including hydrocarbon solvents, for example petroleum fractions such as naphtha, kerosene, diesel and heating oil; aromatic hydrocarbons such as aromatic fractions, eg. those sold under the 'SOLVESSO' tradename; and paraffinic hydrocarbons such as hexane and pentane and isoparaffins.

Further solvents include oligomers and hydrogenated oligomers of alkenes such as hydrogenated decene-1 dimer or trimer. Also useful are alcohols and esters especially higher alcohols such as liquid alkanols having at least eight carbon atoms. An especially useful solvent is isodecanol. Mixtures of such solvents maybe used in order to produce a mutually-compatible solvent system.

The concentrate may contain up to 80% by weight, for example 50%, of solvent.

The concentrate is particularly convenient as a means for incorporating the additive composition into fuel oil where despite the presence of the compound, the co-presence of other desired additives in the composition demands an amount of solvent in order to impart handleability. However, concentrates comprising the compound as sole additive may also be used, especially where small quantities of the compound are required and the equipment present for introduction of the additive lacks the necessary accuracy to measure or handle such small volumes.

Where the fuel oil composition is produced by incorporation of the additive composition or concentrate, the amount used of either of these compositions will be such as to ensure the incorporation to the fuel oil of the requisite amount of the compound. For example, however, where the additive composition or concentrate is used, the amount will usually be in the range of 1 to 5,000 ppm of the composition (active ingredient) by weight per weight of fuel, especially 10 to 2000 ppm such as 50 to 500 ppm.

As indicated above, the compound defined under the first aspect, and the additive composition and concentrate defined under the second aspect, find application in low sulphur fuel oils.

A further aspect of this invention is therefore the use of the compound, or the additive composition or concentrate, in a liquid hydrocarbon middle distillate fuel oil, having a sulphur concentration of 0.2% by weight or less, per weight of fuel, particularly to improve the lubricity thereof. This invention also provides a method for improving the lubricity of a liquid hydrocarbon middle distillate fuel oil having a sulphur concentration of 0.2% by weight based on the weight of fuel, comprising the addition thereto of the additive composition or concentrate, or of the compound.

The Compound of the Third Aspect

The compound claimed under the third aspect comprises one or more hydroxyl derivatives of the formula —OR' wherein R' is as defined in relation to the first aspect but is not hydrogen. Such materials may show good performance as lubricity improvers and as detergents and/or dispersants in low sulphur middle distillate fuel oils.

The invention will now be described further by reference to the examples only as follows:

EXAMPLE 1

Preparation of the Compounds, and the Fuel Oil Composition

Compounds as defined under the first aspect of the invention were prepared via amidification of hydrocarbyl-substituted salicylic acid with various amines.

In each case, the hydrocarbyl substituents on the salicylic acid were n-alkyl groups ranging in carbon number from 14 to 18 and predominately C18 alkyl. Most of the salicylic acid reactant was monoalkylated although a proportion was dialkylated with two such alkyl groups. The amines used in each preparation are shown in Table 1.

The amidification reactions were performed as follows: Reaction of C14–18 alkyl salicylic acid with tetraethylene pentamine (TEPA)

To a 5 necked flask was added 100 g of alkylsalicylic acid (65% active ingredient in xylene) and 100 g of toluene. While being stirred under nitrogen, the mixture was heated up to 80° C. and 16.6 g of TEPA in the dropping funnel was added slowly (over a 15 minute period) to the reaction flask. The mixture was then heated at toluene reflux temperature (110° C.) for 3 hours.

The reaction mixture was then concentrated by boiling off most of the toluene and heated at 150° C. under nitrogen for 1 hour to decompose the salt into the amide and water. The final product had a TAN of 1.4 and a nitrogen content of 5.54% (wt).

Reaction with N,N-dimethyl-1,3-propanediamine

The above procedure is repeated with 26.9 g of the amine. The final product had a TAN of 2.7 and a nitrogen content of 1.67% (wt).

Reaction with Ethane-1,2-diamine

The above reaction is repeated with 52.8 g of the amine. The final product had a TAN of 0.6 and a nitrogen content of 2.16% (wt).

A fourth amide was prepared via an ester intermediate, as described below:

Preparation of the Amide Derivative by Aminolysis of the Methyl Ester of C14–18 Alkyl Salicylic Acid (i) Preparation of the methyl ester of alkyl salicylic acid In a 5 necked round bottom flask equipped with a mechanical stirrer, a nitrogen sparge and a Dean-Stark condenser were placed 329 g of Alkylsalicylic acid (65% active ingredient in xylene), 349 g of methanol and 16.7 g of 90% sulfuric acid. The mixture was refluxed at 65–66° C. for 16.5 hours.

The mixture was concentrated by boiling off 322 ml of methanol leading to a phase separation of the mixture. The reaction mixture was decanted into a separating funnel and the bottom layer, approximately 40 ml consisting of xylene and sulfuric acid, was removed. The top layer was washed 5 times with 100 ml of distilled water and finally dried in a rotary evaporator at 118° C. to give 203 g of material with a TAN of 81.3 mg KOH/g.

(ii) Aminolysis of the ester

In a 5 necked round bottom flask equipped with a mechanical stirrer, a nitrogen sparge and a Dean-Stark condenser were placed 77.5 g of the ester product prepared above, and 296.2 g of Solvent 30. The mixture was heated at 70° C. and 43.7 g of N,N dimethyl-1,3-propanediamine was added over a 10 minute period. The mixture was then brought to reflux temperature (108° C.) and kept there for 13 hours. A part of the solvent and unreacted amine was then boiled off. The mixture was finally rotary evaporated under vacuum at 130° C. to give 90.3 g of a product with a TAN of 74.9 and a nitrogen content of 4.8% (wt).

In all cases the preparations comprised the desired amide product and a proportion of C14–18 alkyl phenol (unreacted from the formation of the salicylic acid).

The amide-containing compositions of Table 1 were added to two low sulphur middle distillate fuel oils having the characteristics show below.

|  | Fuel A | Fuel B |
| --- | --- | --- |
| Sulphur Content (wt %) | 0.02109 | 0.00045 |
| Density (15° C., kg/m³) | 0.8256 | 815.3 |
| D-86 Distillation (° C.) |  |  |
| IBP | 157 | not reported |
| 95% | 328 | 279 | in the amounts shown in Table 2, to provide fuel oil compositions according to the invention.

The fuel oil compositions of Example 1 were tested in the High Frequency Reciprocating Rig Test (or "HFRR") for lubricity performance and compared with the untreated fuel oil (Comparative No 1). The HFRR test method is described in the industry standard test methods CEC PF 06-T-94 and ISO/TC22/SC7/WG6/W188 and was performed at 60° C.

The results of the HFRR tests are shown in Table 2.

In conclusion, it can be seen that fuel oil compositions comprising the compound defined under the first aspect of the invention provide improved lubricity performance.

TABLE 1

| Preparation No. | Amidification Starting Materials | |
| --- | --- | --- |
|  | Acid Precursor | Amine |
| 1 | C$_{14-18}$ alkyl salicylic acid | Mixture of polyethylene polyamines approximating to tetraethylene pentamine |
| 2 | C$_{14-18}$ alkyl salicylic acid | N,N-dimethyl-1,3-propanediamine |
| 3 | C$_{14-18}$ alkyl salicylic acid | Ethane-1,2-diamine |
| 4 | methyl ester of C$_{14-18}$ alkyl salicylic acid | N,N-dimethyl-1,3-propanediamine |

TABLE 2

| Preparation No. | Fuel | Treat Rate of Preparation (ppm wt/wt) | HFRR Result @ 60° C. (wear scar diameter in microns) |
| --- | --- | --- | --- |
| Comparative No. 1 | A | — | 558 |
| 1 | A | 200 | 378 |
| 2 | A | 200 | 373 |
| 3 | A | 200 | 330 |
| 4 | A | 200 | 336 |
| Comparative No. 1 | B | — | 650 |
| 1 | B | 200 | 550 |
| 2 | B | 200 | 601 |
| 3 | B | 200 | 576 |

What is claimed is:

1. A method for improving the lubricity of a liquid hydrocarbon middle distillate fuel oil having a sulphur concentration of 0.2% by weight or by less based on the weight of fuel, comprising adding to a major proportion of said fuel 0.5 to 1000 ppm of a compound comprising one or more substituted aromatic ring systems each of which has as substituents;

(i) one or more aliphatic hydrocarbyl groups having 14 to 36 carbon atoms, and (ii) one or more hydroxyl groups or a hydroxyl derivative of the formula —OR' where R' is hydrocarbyl, alkyleneoxyhydrocarbyl, or poly(alkyleneoxy) hydrocarbyl, alkyleneaminohydrocarbyl or poly(alkyleneamino)hydrocarbyl, and (iii) one or more amide groups derivable from an alkylene diamine or polyalkylene polyamine.

2. The method of claim 1 wherein the compound has the general formula (I):

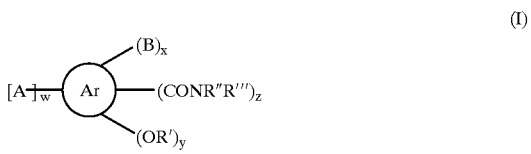

wherein Ar represents an aromatic ring system;

B represents a hydrocarbyl group;

OR' represents a hydroxyl group or a derivative of a hydroxyl group wherein R' may be hydrocarbyl, alkyleneoxyhydrocarbyl or poly(alkyleneoxy) hydrocarbyl, alkyleneaminohydrocarbyl or poly(alkyleneamino) hydrocarbyl.

CONR"R'" represents an amide group wherein R" and R'" each independently represent hydrogen or a hydrocarbyl group or a poly(alkyleneoxy)alkyl or poly(alkyleneamino)alkyl group, optionally substituted by one or more heteroatom-containing groups, and A represents a group of the formula (II):

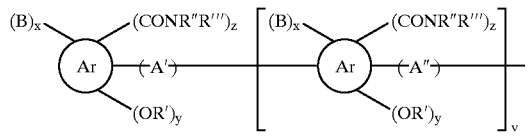

(II)

wherein Ar, B, R', R" and R'" are as defined above, and A' and A" each independently represent hydrocarbylene groups, and wherein v represents an integer in the range of from 0 to 10, w represents an integer in the range of from 0 to 3, and x, y and z each independently represent an integer in the range of from 1 to 3.

3. The method of claim 2 wherein w is 0 and Ar is a benzene ring.

4. The method of claim 1 wherein the ring system is selected from the group consisting of naphthalene, anthracene, phenanthrene, pyrene, azulene, indene, hydroindene, fluorene, diphenylene, biphenyl, quinoline, indole, 2,3-dihydroindole, benzofuran, benzothiophen, carbazole and thiodiphenylamine.

5. The method of claim 1 wherein the fuel oil has 0.05 wt. % or less of sulfur.

* * * * *